United States Patent

Becker

Patent Number: 4,773,908
Date of Patent: Sep. 27, 1988

[54] FILLING TUBE AND SEAL CONSTRUCTION FOR INFLATABLE IMPLANT

[76] Inventor: Hilton Becker, 2584 NW. 23rd Way, Boca Raton, Fla. 33413

[21] Appl. No.: 943,202

[22] Filed: Dec. 18, 1986

[51] Int. Cl.$^4$ .......... A61F 2/12; A61B 17/12; A61B 19/00
[52] U.S. Cl. ...................... 623/8; 128/325; 600/31
[58] Field of Search ............ 623/7, 8, 11; 128/1 R, 128/325, 344, 348.1; 604/96, 99

[56] References Cited

U.S. PATENT DOCUMENTS

| | | | |
|---|---|---|---|
| 3,220,729 | 11/1965 | Whittington | 273/58 |
| 4,085,757 | 4/1978 | Pevsner | 128/344 |
| 4,095,295 | 6/1978 | Lake | 623/8 |
| 4,263,682 | 4/1981 | Bejarano | 623/8 |
| 4,298,997 | 11/1981 | Rybka | 623/8 |
| 4,441,495 | 4/1984 | Hicswa | 128/325 |
| 4,643,733 | 2/1987 | Becker | 623/8 |

*Primary Examiner*—Richard J. Apley
*Assistant Examiner*—David J. Isabella
*Attorney, Agent, or Firm*—Bacon & Thomas

[57] ABSTRACT

An inflatable implant for use in human breast reconstruction includes at least one and preferably two chambers. The chambers are defined by a flexible membrane or lumen and include valves which are adapted to have a singular flexible filling tube passed therethrough for filling the inner chamber.

A dual chambered device includes a viscous gel in the outer chamber. This viscous gel is in contact with the valves and sealingly cooperates with the valves and the filling tube.

The implant also includes at least one valve having a short semi-rigid tube surrounding an opening and extending inwardly of the membrane, i.e. into the chamber. And the filling tube comprises a soft and flexible length of tubing and a solid portion at a distal end thereof. This solid portion has an outer diameter which is slightly larger than the inner diameter of the semi-rigid tube and is stretchable longitudinally to reduce its outer diameter to facilitate passage through the semi-rigid tube. And the solid portion is adapted to sealingly engage the semi-rigid tube upon relaxation thereof.

10 Claims, 2 Drawing Sheets

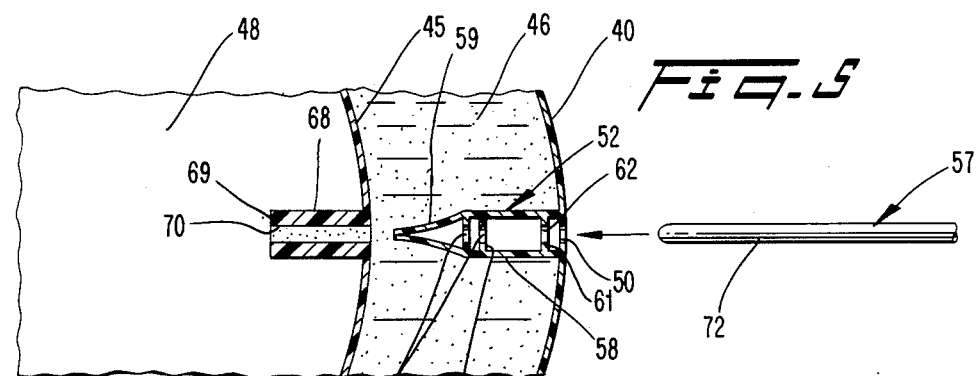
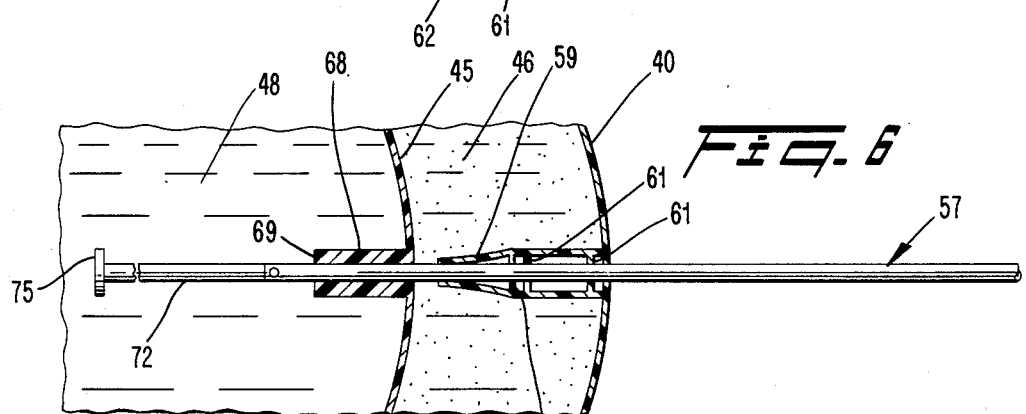
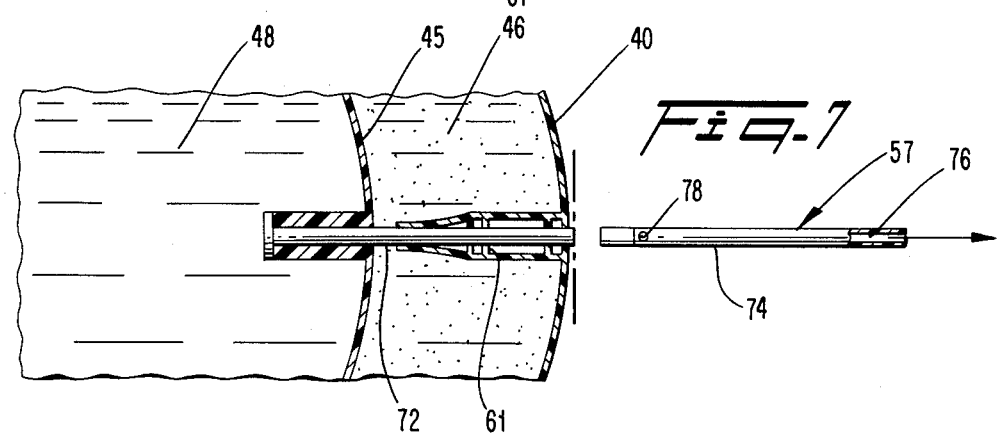
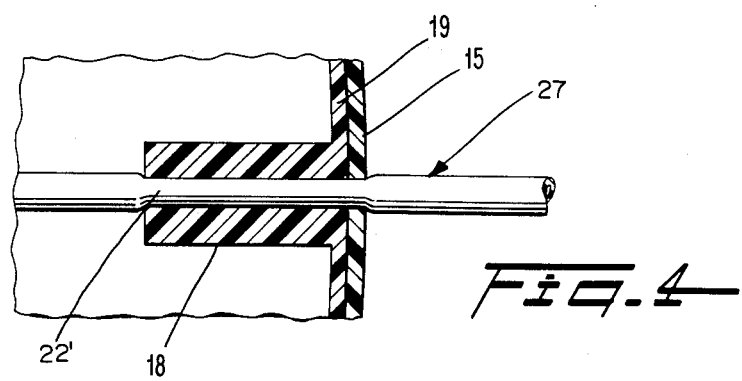

FILLING TUBE AND SEAL CONSTRUCTION FOR INFLATABLE IMPLANT

BACKGROUND OF THE INVENTION

This invention relates to an improved filling tube and seal construction for inflatable implants and more particularly to a filling tube and seal construction for use in inflatable implants used in breast reconstruction. However, it will be understood that this invention may be useful in other types of inflatable implants where it is desired to insure against leakage after implantation and inflation.

Inflatable implants such as those used in breast reconstruction include at least one, and sometimes two soft and pliable members or lumens. The lumens are adapted to be filled with various materials including liquids such as saline, silicone gel, and sometimes both. For example, in my co-pending application Ser. No. 693,890, filed Jan. 23, 1985, and entitled Improved Implant and Inflating Construction, there is disclosed a double lumen implant wherein the outer chamber contains a silicone gel. The inner lumen is filled with a saline solution to inflate the implant to the desired volume. The membranes are unattached from one another, and this, together with the outer viscous gel layer, gives the implant a natural appearance and feel.

The gel in the outer chamber is in contact with both valves thus facilitating seal of the valves when a filling tube has penetrated both valves for an extended period of time (up to three to six months). When the filling tube is removed after such a long period of time, the valves may remain in a distended condition due to stretch caused by the filling tube. Migration of gel between the partially opened valve leaves or flaps is thus of importance in valve closure.

An important feature of these devices resides in the valve used in inflating the implant. One type uses a filling tube which is passed through a valve opening in the membrane to enable delivery of inflating fluid to the membrane interior. In the case of the double membrane implant discussed above, the filling tube passes through valve openings in both membranes and delivers the inflating fluid (saline solution) to the chamber in the inner membrane. Upon completion of the inflation process, the filling tube is withdrawn from both valves. Importantly, the valves reseal upon removal of the filling tube to prevent escape of the fluid.

The valves referred to above are formed in the membranes and are and remain a part of the membrane after the filling sequence is completed. For obvious reasons, e.g., patient comfort, these valves should be small and, as much as possible, be constructed of relatively soft material. However, it is also important that the valve safely and effectively reseal once the filling tube has been withdrawn to prevent loss of fluid from the membrane.

Such valves when constructed of a relatively soft and pliable material satisfy the need that they be comfortable for the patient. However, this can give rise to another problem if the filling tube remains in place for a relatively long period of time, sometimes for several weeks during inflation. In such cases, the valve material may lose its memory and acquire a "set," and therefore not recover its original shape when the filling tube is removed. Also, these implants are often packaged with the filling tube in place in the valve so that there is a higher likelihood of valve leakage because of the sometimes long shelf life of the implant. Thus, there can be a relatively high incidence of leakage in these valves.

In my co-pending application referred to above, the viscosity of the gel material in the chamber between the outer and inner lumens generally is sufficient to insure that gel does not escape the valve in the outer lumen. Sealing of the valve in the inner lumen is also assisted to some extent by the gel. However, the saline solution in the inner chamber is much less viscous than the silicone gel and can leak past the inner valve into the outer chamber if the inner valve does not reseal. In some cases, saline solution entering the outer chamber can leak past the outer valve and escape the implant. In either case, there is a need for a valve for use in this type environment which is soft and pliable and, therefore, comfortable for a patient, and which functions to effectively reseal after removal of an instrument such as a filling tube which has remained in place therein for a relatively long period of time.

In another of my co-pending applications, Ser. No. 06/800,211, filed Nov. 21, 1985, and entitled "Filling Tube Valve Construction for Inflatable Implants." I disclose an improved valve construction. In that application, the valve comprises a length of relatively flexible material having a passage therethrough and joined to the lumen around the inlet opening. The flexible material extends inwardly into the lumen and is normally biased toward a smooth curved configuration which causes the valve passage to close. The valve passage is opened by inserting a filling tube through the passage causing the flexible material to straighten. The flexible material returns to its original curved configuration upon removal of the tube whereupon the valve passage recloses.

The aforementioned valve works well, is useful in both single and multiple lumen prosthesis, adds minimally to the cost of the prosthesis, does not adversely affect the comfort of the patient and aids in preventing leakage.

However, it is presently believed that my new filling tube and seal construction will provide an improved seal over the aforementioned device and will have most, if not all, of the advantage of that device.

SUMMARY OF THE INVENTION

The present invention relates to a filling tube and seal construction for an inflatable prosthesis. The prosthesis includes at least one flexible lumen or chamber which is adapted to be filled with an inflating fluid. The wall of this lumen is made of a membrane and defines an inlet opening through which the lumen is inflated.

A semi-rigid tube surrounds the opening and extends inwardly into the lumen. And, a filling tube including a flexible length of tubing passes through the semi-rigid tube and extends inwardly into the interior of the lumen.

The outer diameter of this filling tube is slightly larger than the inside diameter of the semi-rigid tube. And, the filling tube is stretchable longitudinally to reduce its outer diameter to facilitate the insertion or passage of a distal end of the filling tube through the semi-rigid tube. The filling tube is also adapted to sealingly engage the semi-rigid tube upon relaxation thereof and has at least one opening therein for insertion of fluid into the lumen.

In addition, the distal end of the filling tube which extends into the interior of the prosthesis, defines or forms a solid portion. And after inflation of the lumen, the filling tube is stretched longitudinally and pulled outwardly through the rigid tube until the solid portion thereof is encompassed by the rigid tube to thereby seal the opening when the stretched tube is allowed to relax.

The portion of the filling tube that extends outwardly from the lumen is adapted to be cut off adjacent to the outer end of the semi-rigid tube and forms a relatively smooth surface therewith.

The accompanying drawings, which are incorporated in and constitute a part of this specification, illustrate the preferred embodiments of the invention and, together with the description, serve to explain the principles of the invention.

BRIEF DESCRIPTION OF THE DRAWINGS

FIG. 4 is an enlarged view of the filling tube and sealing construction according to one embodiment of the invention;

FIG. 5 is an enlarged view illustrating a portion of a double lumen inflatable prosthesis embodying a filling tube and seal construction according to a second embodiment of the present invention and shows a filling tube before insertion into the prosthesis;

FIG. 6 is an enlarged view illustrating a portion of the double lumen prosthesis embodying a filling tube and seal construction according to a third embodiment of the invention with a filling tube in position for inflating the prosthesis; and FIG. 7 is an enlarged view of the double lumen prosthesis shown in FIG. 5 but with the filling tube in the sealing position.

DESCRIPTION OF THE PREFERRED EMBODIMENTS

References will now be made in detail to several embodiments of the invention, examples of which are illustrated in the accompanying drawings.

Figure 1:
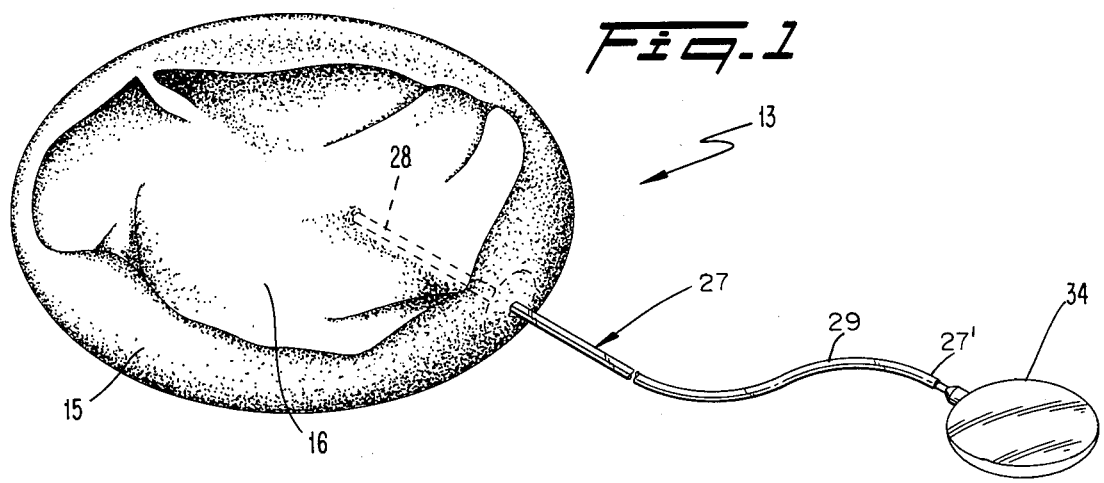
FIG. 1 is a perspective view illustrating a single lumen inflatable prosthesis embodying a preferred form of a filling tube and seal construction according to the present invention and shown with a filling tube and an attached injection dome in place for inflating the prosthesis.
Figure 2:
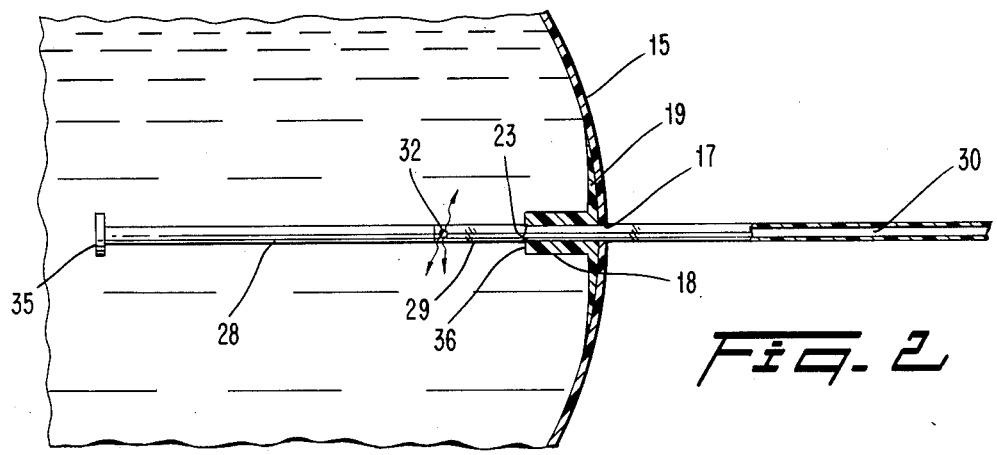
FIG. 2 is an enlarged view of a portion of FIG. 1 showing the filling tube in position for inflating the prosthesis.
Figure 3:
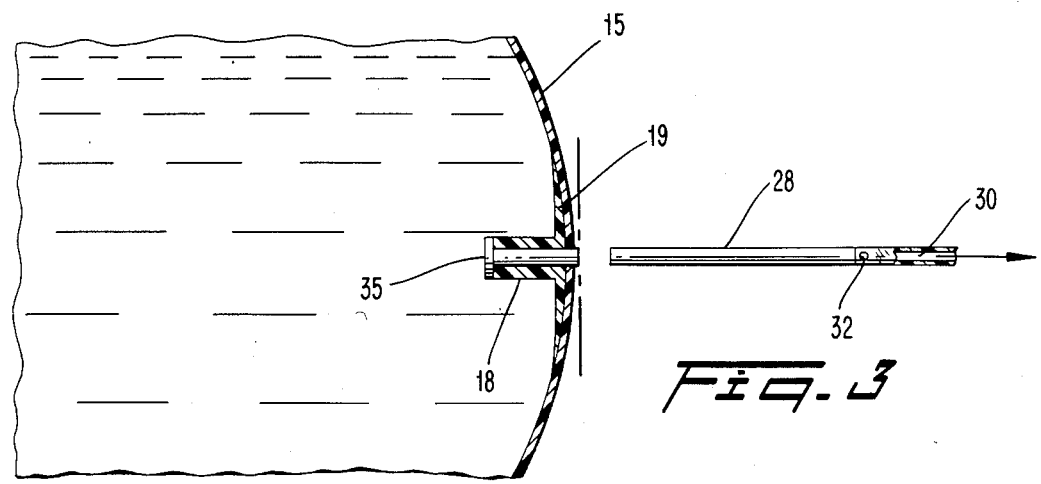
FIG. 3 is an enlarged view of a portion of FIG. 1 showing the filling tube in position for sealing the prosthesis.

A preferred embodiment of the filling tube and seal construction is shown in FIG. 1-3. In accordance with the invention, a filling tube and seal construction is embodied in an inflatable device such as an inflatable implant 13 which includes at least one flexible membrane or lumen 15. The flexible membrane or lumen 15 defines an inflation chamber 16 which is adapted for filling with a fluid to thereby inflate the implant 13. The lumen 15 also defines an inlet opening 17 through which an inflating fluid is delivered (see FIG. 2).

In accordance with the invention, the filling tube and seal construction includes a relatively short semi-rigid tube 18 which has a relatively thick wall with respect to the thickness of the membrane and which surrounds the opening 17. The tube 18 extends inwardly of the lumen 15, and has a passage 23 therethrough which opens inside of the lumen 15.

The lumen 15 is constructed of a suitable material or membrane such as a medical grade silicone elastomer or similar material which does not react with human tissue, as will be understood by those skilled in the art. And, the short semi-rigid tube 18 may be formed of the same or a different material but is preferably formed as an integral part of the membrane and derives its semi-rigid characteristic from the thickness of its wall section. It may also be desirable to form a thicker portion 19 of the lumen 15 as illustrated to further support the tube 18. This thickened portion 19 surrounds the opening 17 and reduces the likelihood of any breaking or tearing of the membrane.

A filling tube 27 constructed of silicone tubing or the like is adapted to pass through the passage 23 which is defined by the relatively short semi-rigid tube 18. The filling tube 27 also includes a solid distal portion 28, which is preferably slightly longer than the length of the semi-rigid tube 18, and a proximal portion 29 which defines a hollow passageway 30 and an opening 32. The opening 32 connects the passageway 30 with the interior of the chamber 16 and operatively connects the interior of the chamber 16 to an injection dome or reservoir 34.

The filling tube 27 is relatively soft so as not to puncture or damage the tube 18 or the lumen 15. This filling tube 27 has an outer diameter which is slightly larger than the inside diameter of the passageway 23 and is stretchable in the longitudinal direction to reduce its outside diameter. Reduction of the outside diameter facilitates the passage of the filling tube 27 through the semirigid tube 18. And the solid portion 28 of the filling tube is adapted to sealingly engage the passageway 23 in the semi-rigid tube 18 upon relaxation from a stretched condition. The use of a stretchable filling tube is also incorporated in a valve construction according to my aforementioned co-pending application Ser. No. 693,890.

In practice, the filling tube may be forced through the passageway 23 by means of a rigid member (not shown) or could be molded into place by having the lumen and semi-rigid tube molded around the filling tube. In the latter case, the filling tube would include an area of reduced diameter so that the inside diameter of the tube 18 would be smaller than the outside diameter of at least the solid portion 28 of the filling tube 27.

The proximal end #27' of the tube 27 is adapted for connection to a fluid source such as the reservoir 34. Fluid such as a saline solution is then forced from the reservoir 34 by means of a hypodermic needle inserted therein (not shown) through the passageway 30 and opening 17 and into the chamber 16. When the chamber 16 is sufficiently filled, the filling tube is stretched longitudinally by pulling and passes through the passageway 23 until the solid distal portion 28 is encompassed by the semi-rigid tube 18. When the pressure or longitudinal extension is released, the solid distal portion returns to its original outside diameter and sealingly engages the semi-rigid tube 18.

In a preferred embodiment of the invention, the solid distal portion 28 includes a generally radially extending flange 35 having a generally T-shaped cross section for engaging a seat 36 on the semi-rigid tube 18. This radially extending flange acts as a stop means and prevents the filling tube 27 from being pulled through the semi-rigid tube 18 and contributes to the reliability of the seal.

Various factors must be considered in constructing the filling tube and seal or valve, such as the thickness of the semi-rigid tube, the stiffness of the materials, the lengths of the semi-rigid tube and the filling tube, their diameters including the nature of the fluids contained within the implant, the pressure of the fluid, etc. Those skilled in the art will appreciate that the seal must not leak and must not cause discomfort to the patient.

FIG. 4 illustrates one embodiment of the invention wherein filling tube 27 is manufactured with a portion 22' of reduced diameter. This further reduction in diameter should minimize any likelihood of leakage during shipment and storage and facilitate forming tubular element 18 around filling tube 27 during the manufacturing operation.

It will also be appreciated that inflatable prosthesis of this type often have the filling tube inserted in place at the time the prosthesis is manufactured and prior to packaging. Thus, the filling tube remains in place during the entire shelf life of the prosthesis which can be for a considerable length of time. A number of previous valves acquired a "set" during this time so that when the prosthesis was implanted, expanded, and the filling tube removed, leakage occurred at the valve. It is presently thought that the present invention will overcome this tendency and as such constitutes an improvement on the valves disclosed in my previous application.

A second embodiment of the invention is illustrated in FIGS. 5–7. As illustrated therein, a double valve is included in a double lumen prosthesis such as the one illustrated and described in my co-pending application Ser. No. 693,890 filed Jan. 23, 1985. That application is hereby incorporated herein by reference, in its entirety.

In that embodiment, the prosthesis includes an outer lumen 40 which is unconnected to an inner lumen 45 so that the lumens are free to move relative to one another for purposes described in detail in the aforementioned application.

A silicon gel is contained in a chamber or space 46 between the lumens 40, 45 and the prosthesis is inflated by means of a saline solution which is delivered to the expansion chamber 48 in the inner lumen 45. The outer lumen 40 is provided with an inlet opening 50 and a valve 52. As described in my co-pending application Ser. No. 693,890, the lumens 40, 45 are manually manipulable to align the valve 52 with a tubular sealing element 68 so that a singular filling tube 57 can be passed through the valve 52 and element 68 for filling the expansion chamber and expanding the implant. Aligning the valve 52 and element 68 is achieved by finger feel location of the element 68 in the inner lumen to align with the valve 52 in the outer lumen.

The valve 52 for the outer lumen 40 is formed of a short tube 58 integral with the lumen 40 and which defines the inlet opening 50. A flap valve 59 extends inwardly of and surrounds the tube 58. The flap 59 is formed in a manner which produces a biasing force causing it to sealingly engage the filling tube 57. Furthermore, the chamber 46 between the lumens 40, 45 is filled with a silicone gel material which helps to seal any gaps between the flap valve 59 and the filling tube 57 which may occur as a result of "set" or deformity of the flaps and helps to effect a proper seal of valve 59 in the same manner as described in my co-pending application Ser. No. 693,890.

In a preferred form, the valve 52 also includes radially extending ribs 61 which extend inwardly from the wall 58 and which define openings 62 therethrough. These openings are adapted to engage the filling tube 57 and have a diameter which is slightly smaller than the outside diameter of filling tube 57.

The inner lumen 45 also includes the relatively short semi-rigid tube 68 which has a relatively thick wall 69 which is relatively thick with respect to the thickness of lumen 45. The tube 68 extends inwardly of the lumen 45 and has a passage 70 therethrough which opens inside of the lumen 45.

The filling tube 57 is adapted to pass through the valve 52 and through the passageway 70 in the semi-rigid tubular element 68. The filling tube 57 includes a solid distal portion 72 which is slightly longer than the distance from the top portion 69 to the opening 50 in the outer lumen 40, and a proximal portion 74 which defines a hollow passageway 76 and an opening 78. The opening 78, illustrated as a small hole, connects the passageway 76 with the interior of the chamber 48.

The filling tube 57 is relatively soft and has an outer diameter which is slightly larger than the inside diameter of the passageway 70 and slightly larger than the diameter of opening 62 in the valve 52. The filling tube 57 is stretchable in its longitudinal direction to reduce its outside diameter to thereby facilitate its passage through the tubular element 68 and valve 52. And, the solid portion 72 of the filling tube 57 is adapted to sealingly engage the interior passage 70 of element 68, the cylindrical flap 59 and ribs 61 of the valve 52 upon relaxation from its stretched condition.

The proximal end of filling tube 57 is adapted for connection to a fluid source (not shown). Then when the filling tube 57 is inserted in the chamber 48 as illustrated in FIG. 6, fluid such as a saline solution is forced through the passageway 76, opening 78 and into the chamber 48.

And when chamber 48 has been inflated to the desired degree, the filling tube 57 is pulled outwardly to thereby stretch the filling tube and reduce its diameter until the solid portion 72 is encompassed by the relatively short semi-rigid tubular element 68 and by valve 52. And when the pulling pressure is released, the solid distal portion returns to its original diameter and sealingly engages the passage 70.

The distal portion 72 also includes a radially extending flange 75 which is adapted to engage a seat 69 on element 68. This arrangement facilitates proper positioning of the filling tube 57 in a sealing position and also tends to improve the seal and reduce the likelihood of any leakage.

Then after completing the seal, the filling tube 57 is cut or severed so that is forms a flush surface with respect to the lumen 40.

It should be understood that the tubular element 68 can be manufactured with radially extending internal ribs as shown in valve 52. However, the prime purpose of this invention is to reduce insofar as possible, any likelihood of leakage of the saline solution from chamber 48 past valve 52 and into the surrounding tissue of a patient. And, it is believed that the construction as illustrated in FIGS. 5, 6 and 7 accomplish this purpose and provide a secure seal.

While the invention has been described with respect to certain embodiments, it will be obvious that various modifications may be contemplated by those skilled in the art without departing from the scope of the invention as hereafter defined by the following claims.

What is claimed is:

1. A filling tube and seal construction for an inflatable implant which includes a flexible membrane defining a chamber and having an inlet opening and a semi-rigid tube surrounding said opening and extending inwardly of said chamber, said filling tube comprising a soft and flexible length of tubing forming a solid portion at a distal end thereof, said solid portion being longer than said semi-rigid tube and the remaining portion of said filling tube defining a hollow passage way and an opening for connecting the interior of said filling tube with the interior of said chamber for inflation of said chamber, and said filling tube having an outer diameter larger than the inner diameter of said semi-rigid tube and being stretchable longitudinally to reduce its outer diameter to facilitate passage through said semi-rigid tube, said solid portion of said filling tube sealingly engaging said semi-rigid tube upon relaxation thereof whereby said filling tube can be stretched longitudinally and moved outwardly through said semi-rigid tube by pulling on a proximal portion of said filling tube after inflation of said chamber to position said solid portion in said semi-rigid tube to seal said opening in said membrane.

2. The construction called for in claim 1 in which said filling tube includes means at the distal end thereof engageable with said semi-rigid tube to limit withdrawal of said filling tube.

3. The construction called for in claim 2 in which said limiting means has a generally T-shaped cross-section.

4. The construction called for in claim 2 in which said distal end means includes a generally radially extending flange engageable with said semi-rigid tube.

5. The construction called for in claim 4 in which said filling tube is made of silicone elastomer.

6. The construction called for in claim 5 in which the membrane and semi-rigid tube are made of silicone elastomer and said semi-rigid tube is formed as an integral part of said membrane.

7. The construction called for in claim 6 in which said membrane includes a thicker portion adjacent said semi-rigid tube to thereby reduce the liklihood of tearing the membrane in that area.

8. An inflatable implant for use in human breast reconstruction comprising inner and outer membranes, said outer membrane containing a viscous gel, first and second valves in said inner and outer membranes respectively and adopted to have a singular filling tube removably passed therethrough for filling said implant, said viscous gel in contact with both of said valves and sealingly cooperating with said valves and with said filling tube when the latter is in place, the improvement comprising a filling tube and seal construction wherein said inner membrane defines a chamber and an inlet opening, and a semi-rigid tube surrounding the opening and extending inwardly of said inner membrane, said filling tube comprising a soft and flexible length of tubing forming a solid portion at a distal end thereof, and said solid portion of said filling tube being longer than said semi-rigid tube and having an diameter larger than the inner diameter of said semi-rigid tube and being stretchable longitudinally to reduce its outer diameter to facilitate passage through said semi-rigid tube, and the remaining portion of said filling tube defining a hollow passage way and an opening for connecting the hollow passage way with the interior of the chamber defined by the inner membrane, said solid portion of said filling tube sealingly engaging said semi-rigid tube upon relaxation thereof whereby said filling tube can be stretched longitudinally and moved outwardly through said semi-rigid tube by pulling on a proximal portion of said filling tube after inflation of the implant to position said solid portion in said semi-rigid tube to seal said opening in said inner membrane.

9. The inflatable implant for human breast reconstruction called for in claim 8 wherein said semi-rigid tube includes sealing means and wherein said filling tube includes a generally radially extending flange which is adapted to engage said sealing means.

10. The inflatable implant for human breast reconstruction called for in claim 9 wherein said inner membrane includes a thickened portion adjacent said semi-rigid tube to thereby reduce the likelihood of tearing the membrane in the area around the semi-rigid tube.

* * * * *